United States Patent [19]

Groman et al.

[11] Patent Number: 4,770,183

[45] Date of Patent: Sep. 13, 1988

[54] BIOLOGICALLY DEGRADABLE SUPERPARAMAGNETIC PARTICLES FOR USE AS NUCLEAR MAGNETIC RESONANCE IMAGING AGENTS

[75] Inventors: Ernest V. Groman, Brookline; Lee Josephson, Arlington, both of Mass.

[73] Assignee: Advanced Magnetics Incorporated, Cambridge, Mass.

[21] Appl. No.: 882,044

[22] Filed: Jul. 3, 1986

[51] Int. Cl.$^4$ .............................................. A61B 6/00
[52] U.S. Cl. .................................... 128/654; 600/12; 424/9
[58] Field of Search ................ 128/1.1, 1.3, 653, 654; 424/9

[56] References Cited

U.S. PATENT DOCUMENTS

| | | |
|---|---|---|
| Re. 27,240 | 11/1971 | London et al. . |
| 2,820,740 | 1/1958 | London et al. . |
| 2,862,920 | 12/1958 | Berger et al. . |
| 2,971,916 | 2/1961 | Schleichter et al. ........ 101/DIG. 13 |
| 3,093,545 | 6/1963 | Westfal et al. . |
| 3,100,202 | 8/1963 | Muller et al. . |
| 3,190,837 | 6/1985 | Brynko et al. ........................ 264/4.4 |
| 3,228,881 | 1/1966 | Thomas . |
| 3,234,209 | 2/1966 | Floramo . |
| 3,275,514 | 9/1966 | Saltman . |
| 3,474,777 | 10/1969 | Figge et al. ........................ 128/1.3 |
| 3,480,555 | 11/1969 | Jackson et al. . |
| 3,531,413 | 9/1970 | Rosensweig . |
| 3,700,595 | 10/1972 | Kaiser . |
| 3,832,457 | 8/1974 | Sugimoto et al. .................... 128/654 |
| 3,843,540 | 10/1974 | Reimers et al. . |
| 3,870,645 | 3/1975 | Frei et al. ............................ 128/654 |
| 3,928,581 | 12/1975 | Dahlberg et al. . |
| 4,001,288 | 1/1977 | Gable et al. . |
| 4,019,994 | 4/1977 | Kelley . |
| 4,025,448 | 5/1977 | Sudol . |
| 4,101,435 | 7/1978 | Hasegawa et al. . |
| 4,136,683 | 1/1979 | Gordon ............................ 128/654 |
| 4,230,685 | 10/1980 | Senyei et al. . |
| 4,247,406 | 1/1981 | Widder et al. . |
| 4,269,826 | 5/1981 | Zimmermann et al. .............. 128/1.3 |
| 4,331,654 | 5/1982 | Morris . |
| 4,345,588 | 2/1982 | Widder et al. . |
| 4,356,098 | 10/1982 | Chagnon . |
| 4,357,259 | 11/1982 | Senyei et al. . |
| 4,452,773 | 6/1984 | Molday ................................ 424/9 |
| 4,501,726 | 2/1985 | Schroder et al. . |
| 4,615,879 | 10/1986 | Runge et al. . |
| 4,637,929 | 1/1987 | Quay . |
| 4,656,026 | 4/1987 | Coffman et al. . |
| 4,675,173 | 6/1987 | Widder . |

FOREIGN PATENT DOCUMENTS

| | | |
|---|---|---|
| 45026 | 10/1961 | Austria . |
| 0160552 | 11/1985 | European Pat. Off. . |
| 0184899 | 6/1986 | European Pat. Off. ................ 424/9 |
| 0186947 | 7/1986 | European Pat. Off. ................ 424/9 |
| 3443251 | 5/1986 | Fed. Rep. of Germany ......... 424/9 |
| 3443252 | 5/1986 | Fed. Rep. of Germany ......... 424/9 |
| 2508802 | 1/1983 | France ................................ 128/1.3 |
| 13098 | 9/1956 | Japan . |
| 7800005 | 12/1978 | PCT Int'l Appl. . |
| 8303920 | 11/1983 | PCT Int'l Appl. . |
| 8402643 | 7/1984 | PCT Int'l Appl. . |
| 8502772 | 7/1985 | PCT Int'l Appl. . |
| 8504330 | 10/1985 | World Int. Prop. O. ............. 424/9 |
| 748024 | 4/1956 | United Kingdom . |
| 2138612 | 10/1984 | United Kingdom . |

OTHER PUBLICATIONS

Saini, S. et al., *Radiology* (1987) 162, 217.

(List continued on next page.)

*Primary Examiner*—C. Fred Rosenbaum
*Assistant Examiner*—Mark F. Colosimo
*Attorney, Agent, or Firm*—Pennie & Edmonds

[57] ABSTRACT

This invention relates to an improved method for obtaining the in vivo MNR image of an organ or tissue of an animal or human subject. More specifically, this invention relates to the use of small (about 10 to about 5,000 angstroms in diameter) biodegradable superparamagnetic metal oxide particles for use as imaging agents. The particles, which may be uncoated or surrounded by a stable polymeric coating, can be mixed with a physiologically acceptable medium to form a uniform dispersoid which can be administered to the subject by a variety of routes. Once administered, the particles collect in the target organ or tissue where they will remain for a time sufficiently long for an image to be obtained, but are ultimately metabolized or cleared within about 7 days.

25 Claims, 3 Drawing Sheets

OTHER PUBLICATIONS

Widder, D. J. et al., *Amer. J. Roentgenol* (1987) 148, 399.
Olsson, M. B. E. et al., *Magnetic Resonance Imaging* (1986) 4, 142.
Weiss, R. D. et al., *J. Appl. Phys.* (1985) 57, 4274.
Welo, L. A.; Baudisch, O. *Chem. Rev.* (1934) 15, 45.
Kaiser, R.; Miskolszy, G. 1970 Intermag Conference, Washington, D.C., Apr. 21–24.
Elmore, W. C. *Physical Rev.* (1938) 54, 1092.
Koch, A. J.; Becker, J. J. *J. Appl. Phys.* (1968) 39, 1261.
Elmore, W. C. *Physical Rev.* (1937) 51, 982.
McKeehan, L. W.; Elmore, W. C. *Physical Rev.* (1934) 46, 226.
Bancroft, W.D. *Appl. Coll. Chem., Gen. Theory*, 3rd Ed. (1932).
Travis, P. M. Mechanochemistry and the Colloid Mill Including the Practical Applications of Fine Dispersion (1928) Book Dept., Chem., Cat. Co., Inc.
Driscoll, C. F. et al. *Microvas. Res.* (1984) 27, 353.
Senyei, A. E. et al. *Metho. Enzymol* (1985) 112, 56.
Ohgushi, M. et al. *J. Magnetic Resonance* (1978) 29, 599.
Renshaw, P. F. et al., *Mag. Resonan. in Medicine* (1986) 3, 217.
Lauffer, R. B. et al., *J. Comput. Assist. Tomography* (1985) 9(3), 431.
Dias, M. H. M.; Lauterbur, P. C. *Mag. Reson. in Medicine* (1986) 3, 328.
Brasch, R. C. *Radiology* (1983) 147, 781.
Wolf, G. L. *Magnetic Resonance Annual* 1985, p. 231.
Weinmann, H. J. et al. *Amer. J. Roentgenol.* (1984) 142.
Runge, P. M. et al., *Radiology* (1983) 147, 789.
Greif, W. L. *Radiology* (1985) 157, 461.
Wesberg, G. E. et al., *Radiology* (1983) 149, 175.
Kaiser, R.; Miskolczy, G. *J. Appl. Phys.* (1970) 41, 1064.
Elmore, W. C. *Physical Rev.* (1938) 54, 309.
Shliomis, M. I., *Sov. Phys. Usp.* (1974) 17, 153.
Cox, J. S. G. et al., *J. Pharm. Pharmac.* (1972) 24, 513.
Marshall, P. R.; Rutherford, D. *J. Coll. Interface Sci.* (1971) 37, 390.
Ricketts, C. R. et al. *Nature* (1965) 5007, 237.
Muller, A. *Arzheim, Forsch.* (1967) 17, 921.
Bersin, T. *Pharm. Acta Helv.* (1964) 39, 657.
Widder, K. J. et al. *Eur. J. Can. Clin. Oncol.* (1983) 19, 135.
Widder, K, et al. *J. Pharm. Sci.* (1979) 68 79.
Molday et al., "Application of Magnetic Microspheres in Labeling and Separation of Cells" in *Nature*, vol. 268, 4 Aug. 1977, pp. 437–438.
Newbauer, "Magnetic Fluids in the Blood" in *IGGG Transactions and Magnetics*, vol. 9, No. 3, Sep. 1973, pp. 447–450.
Gore et al., "Nuclear Magnetic Resonance (NMR) Imaging at Hamersmith Hospital" in *SPIE*, vol. 273, Optical Instrumentation in Medicine (IX), 1981, pp. 8–10.

BIOLOGICALLY DEGRADABLE SUPERPARAMAGNETIC PARTICLES FOR USE AS NUCLEAR MAGNETIC RESONANCE IMAGING AGENTS

1. INTRODUCTION

This invention relates to materials exhibiting certain magnetic and biological properties which make them uniquely suitable for use as nuclear magnetic resonance (NMR) imaging or contrast agents to enhance NMR images of animal organs and tissues. More particularly, the invention relates to the in vivo use of biologically degradable superparamagnetic particles as NMR contrast agents. The particles may be uncoated or surrounded by a non-toxic polymer such as carbohydrate or protein or composites of such polymers. The particles are suspended in physiologically-acceptable carriers to form particle dispersoids. Such dispersoids are administered to animals, including humans, by a variety of routes and the particles therein collect in specific target organs to be imaged. The biodistribution of the particles to target organs or tissues results in a more detailed image of such organs or tissues because the particles, due to their superparamagnetic properties, exert profound effects on the hydrogen nuclei responsible for the NMR image.

The combination of superparamagnetism and biodegradability makes the materials described herein particularly advantageous for use as NMR contrast agents. Superparamagnetism, which results in profound capabilities to alter NMR images, makes it possible to use these materials in concentrations lower than those required for NMR imaging with other types of magnetic materials. Biodegradability results in optimum retention times within the organs and tissues to be imaged, i.e., times sufficient to obtain images conveniently followed by eventual clearance from or degradation within the organ or tissue. Because the materials can be used in lower dosages and because of their biodegradability, the chance of toxic effects from these imaging agents is greatly reduced. These materials can, therefore, be used for a variety of clinical diagnostic purposes including, but not limited to, detection of cancerous lesions in liver and other reticuloendothelial tissue, detection of cancerous or other lesions in the intestine, detection of liver diseases, such as cirrhosis and hepatitis, and assessment of liver regeneration.

2. BACKGROUND OF THE INVENTION

2.1. In vivo NMR Imaging: General Considerations

Nuclear magnetic resonance (NMR) is now widely used for obtaining spatial images of human subjects for clinical diagnosis. Clinical usage of NMR imaging, also called magnetic resonance imaging or, simply, MRI, for diagnostic purposes has been reviewed [see e.g., Pykett, et al., Nuclear Magnetic Resonance, pgs. 157–167 (April, 1982) and T. F. Budinger, et al., Science, pgs. 288–298, (October, 1984)]. Several advantages of using such a procedure over currently used diagnostic methods, e.g., X-ray computer-aided tomography (CT), are generally recognized. For instance, the magnetic fields utilized in a clinical NMR scan are not considered to possess any deleterious effects to human health (see Budinger, supra., at 296). Additionally, while X-ray CT images are formed from the observation of a single parameter, X-ray attenuation, NMR images are a composite of the effects of number of parameters which are analyzed and combined by computer. Choice of the appropriate instrument parameters such as radio frequency (Rf), pulsing and timing can be utilized to enhance (or, conversely, attenuate) the signals of any of the image-producing parameters thereby improving the image quality and providing better anatomical and functional information. Finally, the use of such imaging has, in some cases, proven to be a valuable diagnostic tool as normal and diseased tissue, by virtue of their possessing different parameter values, can be differentiated in the image.

In MRI, the in vivo image of an organ or tissue is obtained by placing a subject in a strong external magnetic field and observing the effect of this field on the magnetic properties of the protons (hydrogen nuclei) of the water contained in and surrounding the organ or tissue. A number of parameters can be measured, but the proton relaxation times, $T_1$ and $T_2$, are of primary importance. $T_1$ (also called the spin-lattice or longitudinal relaxation time) and $T_2$ (also called the spin-spin or transverse relaxation time) depend on the chemical and physical environment of organ or tissue water and are measured using Rf pulsing technique; this information is analyzed as a function of distance by computer which then uses it to generate an image.

The image produced, however, often lacks definition and clarity due to the similarity of the signal from other tissues. In many cases, this eliminates any diagnostic effectiveness, as any signal differences between normal and diseased tissue are ordinarily small. To overcome this drawback, researchers have tried increasing the external magnetic field intensity of the scanning instruments and the use of contrast agents. Increasing the external magnetic field intensity appears to be of limited utility because higher Rf frequencies are used (since the resonant frequency, which is proportional to the external field intensity, is higher) and as this frequency is increased, the depth to which it can penetrate through tissue decreases. Thus, the use of contrast agents appears to be the most promising avenue to pursue.

2.2. MRI Contrast Agents

Contrast agents are substances which exert an effect on the NMR parameters of various chemical species around them. Ordinarily, these effects are strongest on the species closest to the agent, and decrease as the distance from the agent is increased. Thus, the areas closest to the agent will possess NMR parameters which are different from those further away. Proper choice of a contrast agent will, theoretically, result in uptake by only a certain portion of the organ or a certain type of tissue (e.g., diseased tissues), thus providing an enhancement of the contrast which in turn generates a more accurate image.

Since NMR images can be generated from an analysis of the T1 or T2 parameters discussed above, it is desirable to have a contrast agent which affects either or both parameters. Much research has, therefore, centered around two general classes of magnetically active materials, paramagnetic materials (which act primarily to decrease T1) and ferromagnetic materials (which act primarily to decrease T2.

Paramagnetism occurs in materials that contain unpaired electrons which do not interact and are not coupled, such as ions in solution or gases with unpaired electrons. Paramagnetic materials are characterized by a weak magnetic susceptibility, where susceptibility is the degree of response to an applied magnetic field. They become weakly magnetic in the presence of a magnetic field, and rapidly lose such activity (i.e., demagnetize) once the external field is removed. It has long been recognized that the addition of paramagnetic solutes to water causes a decrease in the T1 parameter.

Because of such effects on T1 a number of paramagnetic materials have been used as NMR contrast agents. For example, trivalent gadolinium ($Gd^{3+}$) chelated with diethylene triamine pentaacetic acid (DTPA), or Gd/DTPA as the chelated form is known, has been reported to decrease T1 and enhance the image of the blood brain barrier. [Weinmann, et al., Am. J. Rad, 142, 619 (1984)]. Manganese ($Mn^{2+}$) and ferric iron ($Fe^{3+}$) have also been used as paramagnetic imaging agents [Greif, et al , Radiology 157, 461 (1985); Runge, et al., Radiology 147, 789 (1983); Brasch, Radiology 147, 781 (1983)].

Ferromagnetism, on the other hand, occurs when the unpaired electrons in certain magnetic materials interact, i.e., are highly coupled. Such materials are characterized by high magnetic susceptibilities in the presence of an applied magnetic field, often hundreds to thousands of times greater than those of paramagnetic materials, and retain their magnetic properties even in the absence of a magnetic field, i.e , after the externally applied field has been removed. Unlike paramagnetism, ferromagnetism results only when the unpaired electrons are contained in a crystalline lattice or metallic complex and is not a property of individual molecules like ions in solution or gases. Ferromagnetic materials include metallic iron and certain metal oxides such as gamma-ferric oxide (gamma-$Fe_2O_3$) or magnetite ($Fe_3O_4$). A typical ferromagnetic iron oxide is Pf-2228 (Pfizer Corporation, Minerals, Pigments & Metals Division, New York, N.Y.), which has long been used for magnetic recording; it exhibits virtually pure ferromagnetic properties.

Ferromagnetic materials have been used as NMR contrast agents because of their large effect on T2. This effect has been attributed to their ability to generate nearly static magnetic field inhomogeneities which cause large increases in apparent spin-spin relaxation rate (T2) but have little or no effect on the spin-lattice relaxation of nearby nuclei [Dias and Lautebur, Mag. Res. Med. 3, 328 (1986)]. The basis of such thinking lies in early observations that ferromagnetic materials alter NMR spectroscopy [Drain, Proc. Phys. Soc. 80, 1380 (1962)] and the more recent observation that ferromagnetic magnetite ($Fe_3O_4$) is a T2-specific relaxation agent [Ohgushi, et al., J. Mag. Res., 29, 599 (1978)]. A recently published patent application [WO No. 85/04330 by Jacobsen and Klaveness, assigned to Nyegaard & Co.] claims a variety of ferromagnetic materials as contrast agents.

A major problem with the use of contrast agents for imaging is that many of the paramagnetic and ferromagnetic materials exert toxic effects on biological systems making them inappropriate for in vivo use. For example, the lanthanide element gadolinium (Gd) is quite toxic and, to make it suitable for in vivo use, researchers have chelated it with DTPA. Such a system can be administered intravenously and has been used clinically to demonstrate pathologic alterations of the blood brain barrier and impaired myocardial perfusion [see R. C. Brasch, et al., *American Journal of Roentgenology*, 142, pgs. 625-630 (1984)]. However, it is not as well adapted to other diagnostic uses. For example, in the liver it is absorbed equally well by normal and cancerous cells. Since T1 and T2 of these cells are quite close, no distinction of normal and diseased tissue can be made; thus this material would make a poor hepatic cancer diagnostic agent [see D. H. Carr, et al., *American Journal of Roentgenology*, 143, pgs. 215-224 (1984)].

Not all toxic elements can be rendered non-toxic by this treatment. For example, chelated manganese (Mn) ions prepared in a manner similar to the Gd ones still exert a significant toxic effect on cardiac and liver tissue [see R. A. Slutsky, et al., *Radiology*, 154, pgs. 733-735 (1985)].

A quite different problem is observed with iron (Fe). While less toxic than either Gd or Mn, Fe is preferably bound by high-affinity proteins such as the porphyrins, to form biologically active compounds. It must, therefore, be administered in a form which will allow it to migrate to the tissue in question without being rapidly metabolized. Chelation does not appear to be particularly fruitful in this regard.

Researchers have also tried surrounding particulate magnetically active materials with various polymeric coatings to prevent these problems. For example, Jacobsen and Klaveness (PCT application No. WO 85/04330) disclose the use of ferromagnetic particles coated by a "biotolerable polymer" for NMR imaging; however, a major consequence of this was the production of particles with large diameters (ranging from 0.8 micron to as high as 15 microns); such large particles will, if administered intravascularly tend to clog the capillaries; ordinarily a diameter of 1 micron or less is required to assure passage [see, e.g. *Chem. Pharm. Bull.*, 23, (1975)]. Schroder and Salford (PCT application No. WO 85/02772) suggest that coated magnetite microspheres of approximately 1 micron in diameter can be prepared and used for in vivo imaging; however, this is close to the 1 micron cut-off, and will tend to cause a problem if any non-uniformity in particle size is observed.

A related problem is that of biodegradability. In order to be suitable for in vivo use a material must be stable for a time sufficiently long to permit an image to be taken, but must then be eventually metabolized or cleared from the body. Many types of particulate magnetic materials can be administered to animals at doses below the effective toxic dose and be effective as NMR contrast agents. However, the fate of particulate materials in vivo often involves uptake by the reticuloendothelial system of the liver, spleen and bone marrow. Often, particulate imaging agents have very long lifetimes in the subject animal. In terms of human use, the long lifetime of an imaging agent can be a distinct disadvantage. Given the ability of some non-metabolizable materials such as asbestos to induce cancer after extended exposure, it appears unlikely that non-biodegradable materials will be considered suitable for human use.

Because of the problems inherent with the use of the presently available contrast agents, there exists a real need for new agents adaptable for clinical use. In order to be suitable for in vivo diagnostic use, such agents must combine low toxicity with an array of properties including superior contrasting ability, ease of administration, specific biodistribiution (permitting a variety of organs to be targeted), and a size sufficiently small to permit free circulation through a subject's vascular system (since this will be an important route for delivery of the agent to various organs). Additionally, the agents must be stable in vivo for a sufficient time to permit the clinical study to be accomplished, yet be capable of being ultimately metabolized and/or excreted by the subject.

2.3. Superparamagnetism

Superparamagnetic materials possess some properties characteristic of paramagnetic materials and some properties characteristic of ferromagnetic materials. Like paramagnetic particles, superparamagnetic particles rapidly lose their magnetic properties in the absence of an applied magnetic field; yet they also possess the high magnetic susceptibility found in ferromagnetic materials. Iron oxides such as magnetite or gamma ferric oxide exhibit superparamagnetism when the crystal diameter falls significantly below that of ferromagnetic materials.

For cubic magnetite ($Fe_3O_4$) this cut-off is a crystal diameter of about 300 angstroms [Dunlop, J. Geophys. Rev. 78 1780 (1972)]. A similar cut-off applies for gamma ferric oxide [Bate in *Ferromagnetic Materials*, vol. 2, Wohlfarth (ed.) (1980) p. 439]. Since iron oxide crystals are generally not of a single uniform size, the average size of purely ferromagnetic iron oxides is substantially larger than the cut-off of 300 angstroms (0.03 microns). For example, when gamma ferric oxide is used as a ferromagnetic material in magnetic recording, (Pfizer Corp. Pf 2228), particles are needle-like and about 0.35 microns long and 0.06 microns thick. Other ferromagnetic particles for data recording are between 0.1 and 10 microns in length [Jorgensen, *The Complete Handbook of Magnetic Recording*, p. 35 (1980)]. For a given type of crystal, preparations of purely ferromagnetic particles have average dimensions many times larger than preparations of superparamagnetic particles.

The theoretical basis of superparamagnetism has been described in detail by Bean and Livingston [*J. Applied Physics, Supplement* to *volume* 30, 1205 (1959)]. Fundamental to the theory of superparamagnetic materials is the destabilizing effect of temperature on their magnetism. Thermal energy prevents the alignment of the magnetic moments present in superparamagnetic particles. After the removal of an applied magnetic field, the magnetic moments of superparamagnetic materials still exist but they are in rapid motion. Temperature also limits the magnetization of superparamagnetaic materials produced by an applied magnetic field. At the temperatures of biological systems and in the applied magnetic fields of NMR imagers, superparamagnetic materials are less magnetic than their ferromagnetic counterparts. For example, Berkowitz, et al. (J. App. Phys. 39, 1261 (1968)] have noted decreased magnetism of small superparamagnetic iron oxides. This may in part explain why workers in the field of NMR imaging have looked to ferromagnetic materials as contrast agents on the theory that the more magnetic a material is per gram, the more effective that material should be in depressing T2 [Drain, Proc. Phys. Soc. 80, 1380 (1962); Dias and Lautebur, Mag. Res. Med. 3, 328 (1986)].

3. SUMMARY OF INVENTION

It is an objective of this invention to provide an in vivo NMR imaging technique for diagnostic purposes which allows for the production of a clear, well-defined NMR image of a target organ. Specifically, it is an objective of this invention to provide an improved imaging method using NMR contrast agents which overcome problems of toxicity and excessively long retention in the organism, which are easily administered, which distribute in vivo to specific organs or tissues, which exert a significant effect on the image produced, and which are biologically degradable.

This invention provides a novel NMR imaging method using biodegradable sub-micron sized superparamagnetic metal oxide particles as contrast agents which fulfill the foregoing objectives. Such particles, it has been discovered, combine an optimal balance of features and are particularly suited for use as such agents. Remarkably, it has been found that these superparamagnetic materials exert a more profound effect on $T_2$ than equivalent quantities of ferromagnetic materials (see e.g., FIG. 1). This is especially surprising since superparamagnetic materials, which are less magnetic than ferromagnetic materials at physiological temperatures and in the applied magnetic fields of NMR imagers, would be expected to be less effective than ferromagnetic materials in depressing T2. It has also been surprisingly found that the particles used in the invention exhibit highly advantageous behavior with regard to biodegradability, making them extremely practical and safe contrast agents: they remain in the target organ or tissue, as evidenced by their T2 depressing effect, long enough for convenient imaging yet they are biologically degraded or cleared, as evidenced by the loss of T2 depression, within about a week, i.e., about seven days. Additionally, the particles are sufficiently small to permit free circulation through the subject's vascular system and rapid absorption by the organ/tissue being imaged. Finally, due to their superparamagnetic properties, such particles are easy to handle as they resist clumping after removal of an external magnetic field.

The superparamagnetic particles, which are comprised of sub-micron sized metal oxide crystalline cores, may be uncoated or coated with a polysaccharide, a protein, or a composite thereof. By way of illustration, the polysaccharide coating may comprise dextran of varying molecular weights and the protein coating may comprise bovine or human serum albumin. In the case of coated particles, it has been discovered that, remarkably, the coatings can serve a dual purpose, encouraging the uptake of the coated particles by cells in the target organ and preventing these cells from metabolizing and excreting the magnetic core too rapidly (i.e., permitting a sufficiently long residence time in the tissue for convenient imaging but not so long as to result in long term toxicity problems).

Each individual superparamagnetic particle is comprised of a small (about 10 to about 500 angstroms in diameter) metal oxide crystalline core, such core being preferably composed of magnetically active metals. The overall particle size for each can range from about 10 to about 5,000 angstroms, including coatings, if present. Preferred superparamagnetic particles comprise iron oxides with crystal sizes ranging from about 50 to about 500 angstroms. These iron oxide particles have surface areas greater than 75 $m^2$/gram. In aqueous solution, these iron oxide particles have a size range between about 50 and about 5,000 angstroms, including coatings, if any. The superparamagnetic iron oxides have magnetic saturations between about 5 and about 50 electromagnetic units (EMU) per gram of oxide and possess a magnetic squareness of less than 0.10, i.e., lose greater than 90% of their magnetism when the applied magnetic field is removed.

Superparamagnetic particles with these general dimensions overcome problems associated with the use of ferromagnetic and paramagnetic materials as NMR contrast agents. Specifically, superparamagnetic particles, because they are smaller than ferromagnetic particles, are not necessarily exclusively taken up by the subject's reticuloendothelial cells but may be targeted to other organ and tissue sites with the body. Also, because the superparamagnetic particles are smaller than ferromagnetic particles, they have higher surface area per unit mass and are more easily and rapidly digested by chemical or metabolic processes. However, the superparamagnetic particles used herein, because they are larger than paramagnetic ions, are not so rapidly metabolized in the target organ or tissue as to prevent convenient imaging.

Uncoated or coated particles may be suspended in an appropriate medium (e.g., saline) to form a particle dispersoid. This dispersoid is not in the form of a particulate suspension but rather is in the form of translucent liquid, the shade of which varies with the concentration of magnetic particles.

This dispersoid may be administered to the subject being studied. Depending on the route of administration, the particles are distributed to various target organs, where absorption occurs. For example, when the superparamagnetic particles are administered intravascularly (e.g., intravenously or intra-arterially), they are selectively distributed to reticuloendothelial organs, including liver, spleen, lymph nodes and bone marrow and, to a lesser extent, lung. However, when the superparamagnetic particles are administered via the gastrointestinal tract, e.g., orally, by intubation or by enema, they can be used as imaging agents for the organs and tissues of the gastrointestinal tract.

The use of sub-micron sized particles is particularly important when the route of administration is intra-vascular, as such particles can freely circulate in the organism's vascular system, since they are small enough to pass through the capillary network. Thus, such contrast agents can be carried to targeted organs or tissue after being intravenously administered with a minimum of trouble or delay.

In one embodiment, a dextran-coated iron oxide particle dispersoid is injected into a patient's bloodstream and the particles localize in the liver. The particles are absorbed by the reticuloendothelial cells of the liver by phagocytic uptake; a particular benefit of this mode of uptake is that phagocytized iron is metabolized and cleared from the liver much more slowly (but not so slowly as to lead to undesirably long retention times) than prior art paramagnetic ions, which tend to agglomerate in the presence of electrolytes (such agglomerates are rapidly excreted by these cells). Additionally, the dextran-coated particles can be preferentially absorbed by healthy cells, with less uptake into cancerous [tumor] cells. This preferential uptake enhances the contrast between healthy and cancerous tissue and allows for better definition of the tumor location on the image.

The images themselves are generated by computer and are a composite mainly comprised of the spin-lattice relaxation time (T1) and the spin-spin relaxation time (T2) of the protons (hydrogen nuclei) comprising the water in the organ tissue. The superparamagnetic particles act primarily to enhance T2 relaxation, but T1 is also affected (although to a lesser extent). By appropriate choice of instrument parameters, a T2-weighted image of the liver (or other target organ or tissue) can be generated in which contrast is enhanced sufficiently to distinguish structural features and, as described above, to localize tumor cells or other diseased tissue.

The coating on the particles can be varied to optimize both the uptake and residence time in the target organ. Specifically, variations in the coating compositions will permit the complexes to remain in the target organ for an extended period of time ranging from approximately one day to about a week, thus permitting several sequential imaging trials to be conducted. It is further contemplated that uptake by the target organ can be stimulated by the attachment of various functional groups to the coating. Such functional groups can be selected from an array of compounds including proteins, polysaccharrides, etc., and should be a group which is recognized and taken up preferentially by the target organ or tissue cells. This affords maximum flexibility since, by proper choice of coating, organs and tissues other than those of the reticuloendothelial system and gastrointestinal tract can be targeted and imaged. Thus, these particles can serve as valuable tools for an assortment of diagnostic and research purposes.

4. BRIEF DESCRIPTION OF THE FIGURES

2A and 2B were obtained without the use of contrast agents and were taken at different settings of instrument.

2C and 2D were obtained after the intravenous administration of the dextran-coated particle produced in Example 6.1. at a dosage of 0.5 mg/kg; the tumor can clearly be seen.

2E is the image reproduced in 2C showing the tumor highlighted by crosshairs.

Figure 3:
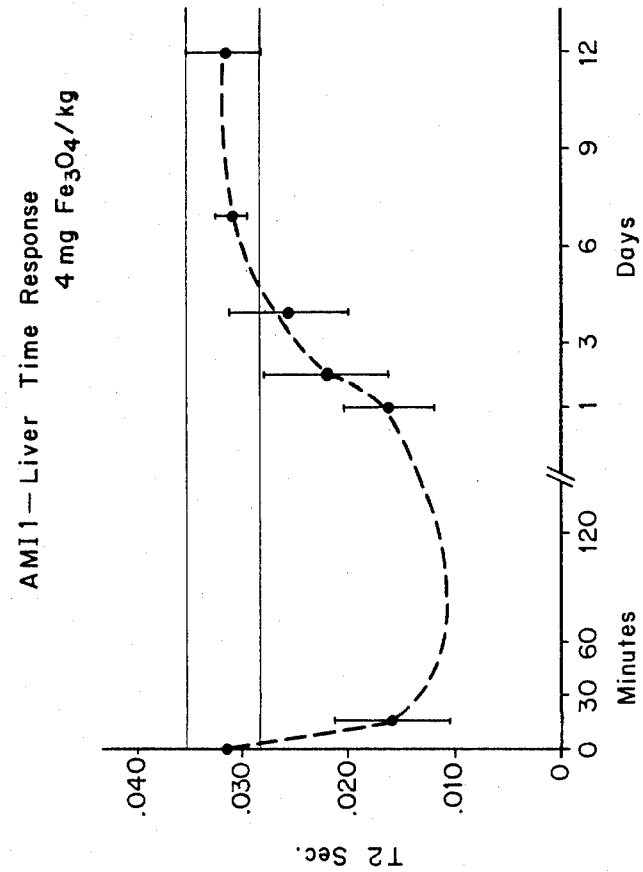

FIG. 3 shows the retention time of the dextrancoated particle of Section 6.1.

5. DETAILED DESCRIPTION OF INVENTION

5.1. Preparation of Coated Superparamagnetic Iron Oxide Particles

The synthesis of superparamagnetic iron oxide particles for use as MRI contrast agents is accomplished by mixing ferrous and ferric salts with base to form a black, magnetic oxide of iron. Crystals result from such precipitations, for when the material is subjected to X-ray diffraction analyses long range order is apparent. A diameter of between about 50 and about 300 angstroms for such crystals has been calculated although crystals may range in diameter from about 10 to about 500 angstroms. The iron oxides have correspondingly high surface areas, greater than about 75 $m^2/gm$.

The presence of ferrous salts prior to base addition insures the formation of a black, crystalline magnetic iron oxide. Without the ferrous ion, paramagnetic ferric oxide gels (noncrystalline materials) result (as described in U.S. Pat. No. 2,885,393). The presence of divalent iron, so essential to the formation of the superparamagnetic material, can then be removed by exposure of the material to oxygen. Oxidation of the iron to produce gamma $Fe_2O_3$ after formation of the crystal does not alter the usefulness of the material as a contrast agent in MRI or the superparamagnetism.

It is to be understood throughout this detailed description, that the use of superparamagnetic iron oxides as NMR contrast agents is but one embodiment of the invention and that superparamagnetic oxides of other magnetic metals, e.g., cobalt or gadolinium, may be substituted for iron oxides.

There are two general strategies for the formation of the coated superparamagnetic iron oxide particles suitable for MRI.

1. Synthesis of iron oxide by precipitation in the presence of polymers like dextran, or polyglutaraldehyde or other material. Such syntheses include those described by London et al., U.S. Pat. No. 2,870,740, Molday, U.S. Pat. No. 4,452,773, Cox et al., *Nature*, 208, 237 (1965) and Rembaum, U.S. Pat. No. 4,267,234; all of which are incorporated herein by reference.

2. Synthesis of the iron oxide by precipitation followed by coating with a polymer like dextran or other material. This type of synthetic route is utilized by Elmore, *Phys. Rev.* 54, 309 (1938) and Ohgushi et al., *J. Mag Res.*, 29, 599 (1978); both of which are incorporated herein by reference.

With proteins and dextrans, synthesis of the oxide in the presence of the polymer seems to effect a tight association between the polymer and the oxide. The synthesis of oxide first, followed by exposure to a protein yields a protein coated particle with the protein being held to the particle surface by weak adsorption phenomena. However, if the oxide and adsorbed polymer can be manipulated, stored and injected in the presence of nonadsorbed polymer, the weakness of the association between oxide and polymer is not a problem. When the particles of Section 6.3. (uncoated) are diluted 1:1 into a neutral buffer containing 1% w/v human serum albumin (HSA), considerable protein will adsorb to the oxide surface. This approach to the synthesis of an albumin coated magnetic particle is a practical one for an imaging agent. The HSA coated particle (plus HSA in solution) can be injected into a patient and the HSA in solution mixes with HSA in serum. When particles are made by this approach the loosely associated HSA can be removed by treatments such as moderate temperature (50° C.) or high salt (1M NaCl).

The coating methods are general and can be performed with a variety of physiologically acceptable proteins and carbohydrates, particularly those with molecular weights from about 5,000 to about 250,000 daltons. Other polymeric coatings include, but are not limited to, albumin/dextran composites, ficoll, dextrin, starch, glycogen and polyethylene glycol.

5.1.1. Preparation of Polysaccharide-Coated Particles

Polysaccharide-coated superparamagnetic iron oxide particles (about 10 to about 5000 angstroms in diameter) useful as NMR contrast agents are prepared by a single-step process according to the procedure of Molday [U.S. Pat. No. 4,452,773] incorporated herein by reference above. In a preferred embodiment, dextranized divalent ($Fe^{2+}$) and trivalent ($Fe^{3+}$) iron salts, e.g., $FeCl_2$ and $FeCl_3$, are precipitated from an aqueous solution containing a mixture of the iron salts and dextran (molecular weight of dextran can vary from 5,000 to 250,000 daltons) by the dropwise addition (to pH=10) of base, ammonium hydroxide ($NH_4OH$) at 60°-65° C., followed by centrifugation at $1500 \times g$ for 15 minutes to remove the oversized particles which are subsequently discarded. The remaining particles are dialyzed against distilled water and can be concentrated by ultrafiltration. Any unbound dextran can be removed by gel filtration chromatography in a chloride/acetate buffer.

The ratio of $Fe^{3+}$ to $Fe^{2+}$ is preferentially maintained at about 2:1, but can be varied from about 0.5:1 to about 4.0:1 without substantial changes in product quality and efficiency as contrast agents.

Likewise, bases other than ammonium hydroxide ($NH_4OH$) can be used, but $NH_4OH$ is preferred because the ammonium ion has a slight dispersing effect on iron oxides which increases the yield.

As mentioned above, various magnetically active metals notably colbalt Co, and gadolinium Gd, may be substituted for iron Fe, without any deleterious effect on the efficiency of the particles as contrast agents. Use of other polysaccharides such as starches, glycogen or dextrins is also contemplated.

5.1.2. Preparation of Protein-Coated Particles

Protein-coated superparamagnetic iron oxide particles are prepared by a single-step process similar to that of Molday [U.S. Pat. No. 4,452,733]. The protein-coated particles can be prepared like the dextran coated wherein the iron salts (e.g., $FeCl_2$ and $FeCl_3$) and the protein are dissolved in water and the coated iron oxide particles are precipitated by the dropwise addition of base, ammonium hydroxide ($NH_4OH$) to pH=10. In an alternative embodiment the protein can be dissolved in the base and an aqueous solution of the iron salts can be added dropwise to form a coated particle.

In either method, the oversized particles are subsequently collected by centrifugation at $1500 \times g$ and the remaining particles are subjected to dialysis against distilled water followed by ultrafiltration. Any unbound protein can be removed by gel filtration chromatography in a chloride/acetate buffer.

As with the polysaccharide coated particles, both the coating composition and the $Fe^{3+}/Fe^{2+}$ ratio (about 2/1) can be varied from about 0.5:1 to about 4:1 without any deleterious effect on the efficiency of these particles as contrast agents.

As mentioned above, various magnetically active metals notably cobalt Co, and gadolinium Gd, may be substituted for iron Fe, without any deleterious effect on the efficiency of the particles as contrast agents.

5.1.3. Preparation of Uncoated Particles

Uncoated ferrous oxide (FeO) and ferric oxide ($Fe_2O_3$) superparamagnetic particles are prepared by mixing an aqueous solution of ferric chloride ($FeCl_3$) with ferrous chloride ($FeCl_2$) in hydrochloric acid (HCl) and precipitating in 0.7 molar aqueous ammonia. The base precipitation offers a dual advantage in that the base also oxidizes the chlorides to form FeO and $Fe_2O_3$. The precipitate (a gelatinous substance) is then collected by centrifugation or application of a magnetic field followed by decantation of the liquid phase.

The gel is then peptized to form a dispersoid by mixing with either 1 molar aqueous tetramethylammonium hydroxide (to form an alkaline dispersoid) or 2 molar aqueous perchloric acid (to form an acidic dispersoid) followed by centrifugation and redispersion in water. Both of these dispersoids show remarkable stability and, being colloidal in nature, will not possess large solid particles. The counterions, either tetramethlylammonium hydroxide or perchlorate, are charged in basic or acidic media, respectively and, thus, prevent complex coagulation in solution; the particles (complexes of iron oxide/counterions) can be repeatedly precipitated and re-dispersed in solution and will retain this property.

In an alternative embodiment the particles can be collected by the application of an external magnetic field rather than centrifugation. The resultant magnetic cake is then peptized by the appropriate counterion.

The ratio of $Fe^{3+}/Fe^{2+}$ is preferably maintained at about 2/1, but can be varied between about 0.5/1 and about 4.0/1. Decreasing the ratio will produce larger and increasing the ratio will produce smaller sized "particles". Additionally, the size is strongly dependent on the pH of the ammonia in the initial precipitation and any increase in pH will produce a smaller particle. Using the 2/1 ratio and 0.7M $NH_4OH$, the average particle size produced is 120 angstroms as measured on a coulter particle size analyzer.

5.2. Use of the Particles as NMR Imaging Agents

The magnetic materials described above can be used as contrast-enhancing agents for in vivo NMR imaging. In one embodiment, the particles are dispersed in a suitable injection medium, such as distilled water or normal saline, to form a dispersoid which is introduced into the subject's vascular system by intravenous injection. The particles are then carried through the vascular system to the target organ where they are taken up.

When intravascularly administered, the particles will be preferentially taken up by organs which ordinarily function to cleanse the blood of impurities, notably the liver, spleen, and lymph nodes, and the other organs which tend to accumulate such impurities, notably bone and neural tissue and to some extent, lung. In each of these organs and tissues, the uptake into the reticuloendothelial cells will occur by phagocytosis, wherein the particles enter the individual cells in membrane-bound vesicles; this permits a longer half-life in the cells, as such membrane-bound particles will not tend to clump or aggregate (aggregates are rapidly metabolized and cleared from the organ/tissue). Other uptake mechanisms are possible, e.g., pinocytosis. Also, it is possible that the other cells of the liver (hepatocytes) may absorb the magnetic particles.

Because cancerous tumor cells can lack the ability of phagocytic uptake, the intravascularly administered particles can serve as valuable tools in the diagnosis of cancer in the above-mentioned organs, as tumors will be immediately distinguishable on any image obtained.

In a another embodiment, the particles are administered as dispersoids into the gastrointestinal tract, which includes the esophagus, stomach, large and small intestine, either orally, by intubation, or by enema, in a suitable medium such as distilled water or any of the mixtures listed in Table III of Example 6.7. The particles are preferentially absorbed by the cells of the tract, especially those of the intestine and, like the intravascularly introduced particles will exert an effect on T2 of the organ or tissue. In this manner, cancers and other debilitating diseases of the digestive system such as ulcers can be diagnosed and affected areas pinpointed.

Regardless of the route, once administered, the particles distribute to and collect rapidly in the target organs, generally in 30-minutes to an hour and, depending on the coating used, the contrast effects may last up to about 7 days. In the organ, these superparamagnetic particles will generate a magnetic field when exposed to the external field of the NMR imager. These newly-generated fields will exert an effect on the magnetic moments of the hydrogen nuclei (protons) in neighboring molecules; notably affected is the spin-spin relaxation time, T2. When this parameter is measured, the protons nearest the agent will have values quite different from those further away. Thus, the contrast is enhanced between areas which absorb the particles rapidly and those which absorb them slowly or not at all.

The differences in parameter values are interpreted by computer and used to generate an image of the organ in question. In the cases, as mentioned above, where uptake occurs by phagocytic processes (notably the liver, spleen, lymph nodes, and bone and neural tissue and to some extent, lung) such an image will clearly and distinctly differentiate between cancerous and healthy tissue, allowing for tumor location. In other organs and/or in the diagnosis of other diseases, modifications of the coating of these particles by the attachment of various functional groups will stimulate uptake by the organ or cell of choice. For example antibodies to a particular tumor cell (e.g. lung carcinoma) can be attached to the surface of a coated particle, stimulating uptake by that organ if such a cell is present. In this way, the method can serve as a diagnostic tool for many diseases.

6. EXAMPLES

6.1. Preparation of Dextran-Coated Particles

To a solution of 500 mls of 0.28M $FeCl_3$, 0.16M $FeCl_2$ and 12.5% w/v dextran, (molecular weight 71,000 daltons from Sigma Chemical Company, Cat. #D1390) is added 500 mls 7.5% $NH_4OH$ over a 2 minute period. A black, magnetic solid forms comprised of large and small particles. The material is stirred for 5 minutes and then heated for 30 minutes at 70° C. The solution is centrifuged for 1500×g for 15 minutes to remove large particles, and the small particles are dialyzed against 10 gallons of $H_2O$ for three days changing the water each day.

The resultant particles exhibit a diameter of 1400 angstroms as measured on a Coulter N4 particle size analyzer.

6.2. Preparation of Particles Coated with Bovine Serum Albumin

To a solution of 80 mls of 0.5% bovine serum albumin (BSA), 0.27M $FeCl_3$, and 0.16M $FeCl_2$, is added 80 mls of 7.5% $NH_4OH$. A black, magnetic solid forms comprised of particles. The mixture is allowed to stand for 5 minutes and then centrifuged at 1,500×g for 15 minutes to remove larger particles. The pellet is discarded and the supernatant placed in a dialysis bag and dialyzed against 3 changes of 10 gallons of distilled water. Larger particles are again removed by centrifugation as above and discarded. Particles are then concentrated by ultrafiltration using an XM-50 membrane and a stirred cell filtration device from Amicon Corporation, Lexington, Mass.

The resultant particles exhibit a diameter of 1730 angstroms as measured on a Coulter N4 particle size analyzer.

6.3. Preparation of Uncoated Particles

One hundred milliliters of solution of 0.8M $FeCl_3$, 0.4M $FeCl_2$ and 0.4M HCl is added dropwise to 1000 ml of 2.4% $NH_4OH$ and mixed for 5 minutes. A black, magnetic solid forms comprised of easily visible particles. For particles to be visible, they must be larger than the wavelength of scattered light which is about 500 nm (0.5 microns). The particles are isolated by attracting them to a permanent magnet on the outside of the reaction vessel and the solution decanted. To the magnetic cake is added 55 mls of 50% triethylamine in water. Smaller particles are created. The mixture is dialyzed overnight against water which causes the large particles to reappear. Just enough triethylamine is then added to again create the smaller particles resulting from the addition of triethylamine. The particles are then filtered through a 0.2 micron filter indicating the final material is below this size.

6.4. Use of Particles in Liver Tumor Visualization

The effect of the dextran-coated particles of Section 6.1. on the image of a rat liver tumor is demonstrated in FIG. 2, which presents reproductions of 5 images obtained on a Technicare NMR imager. The images in 2A and 2B were obtained prior to the introduction of the imaging agent using different imager settings. In neither case can the tumor be clearly seen. 2C and 2D are images of the same rat liver and were obtained after a single 0.5 mg/kg dose of the Section 6.1. dextran-coated particle by intravenous injection through the tail vein. The tumor is easily seen and the overall size and shape can be gauged; in 2E the tumor is marked by cross-hairs to aid in visualization.

6.5. Comparative Effect on Superparamagnetic Particles and Ferromagnetic Particles on T2

Figure 1:
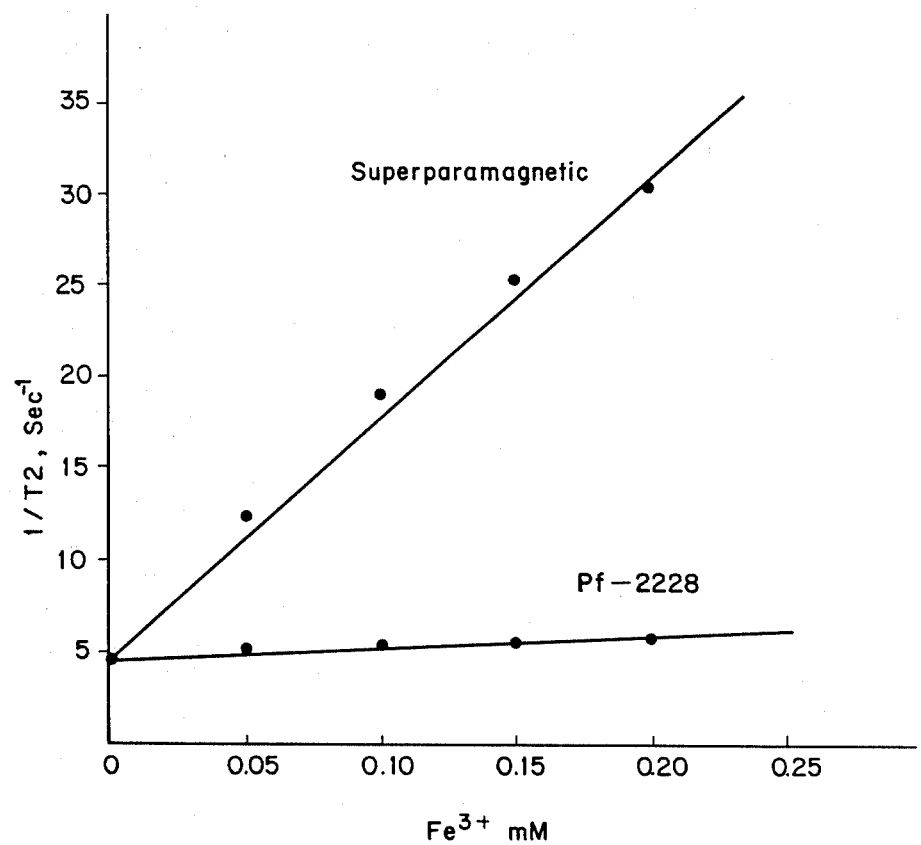
FIG. 1 is a graphical representation comparing the effect of ferromagnetic and superparamagnetic contrast agents on T2.
Figure 2A:
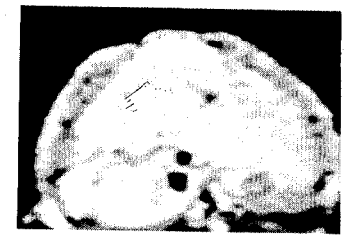
FIG. 2 is a composite of 5 in vivo NMR images of a cancerous rat liver obtained on a Technicare NMR Imager.
Figure 2B:
Figure 2C:
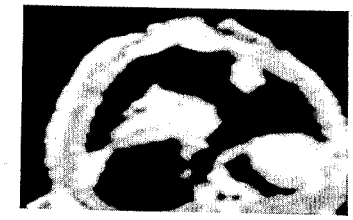
Figure 2D:
Figure 2E:

FIG. 1 compares the T2 of agar gel in the presence of dextran-coated particles (produced in Example 6.1.) and the ferromagnetic particle Pf-2228 (Pfizer). The relaxation times in the presence of varying concentrations of each particle, were determined on an IBM PC-20 NMR spectrometer at 0.47 Tesla (4700 Gauss). It can clearly be seen that the superparamagnetic particle produces a much greater effect on the T2 than the ferromagnetic particle. Given the fact that superparamagnetic materials are much less magnetic than ferromagnetic materials, this result is quite surprising.

6.6. Biodegradability of Dextran-Coated Particles

The dextran-coated particle produced in Section 6.1., identified as AMI-1, was intravenously injected into Sprague-Dawley rats at a dosage of 4 mg $Fe_3O_4$/kg of body weight (in a distilled water carrier). Periodically, the rats were sacrificed, and T2 of the liver tissue was measured on an IBM PC-20 NMR Spectrometer. The results are presented in FIG. 3.

The data demonstrate that T2 undergoes a marked drop within 30 minutes after the injection, and then begins to recover slowly, attaining nearly ⅔ its original value within 72 hours and showing complete recovery after 1 week. Thus, the dextran-coated particles are rapidly metabolized and cleared, exhibiting no residual effect after 1 week.

6.7. Biodistribution of BSA-Coated Particles

Six 200 gm Sprague - Dawley rats were injected intravenously with 0.4 mg of the BSA-coated particle (produced in Section 6.2.) in distilled water. Two rats each were sacrificed at 90 minutes, 24 hours, and 7 days after injection and the relaxation times (T1 and T2 of various organs were measured on an IBM PC-20 NMR Spectrometer. The following results were obtained:

TABLE I

Distribution of BSA-Coated Particle in Rat Organs and Tissues

| Time After Injection | | Relaxation Times (msec) | | | |
|---|---|---|---|---|---|
| | | Liver | Spleen | Lung | Blood |
| Control | $T_1$ | 0.279 | 0.544 | 0.688 | 0.786 |
| $N^1 = 6$ | $T_2$ | 32 | 48.3 | 57 | 158 |
| 90 min | $T_1$ | 0.232 | 0.396 | 0.656 | 0.901 |
| N = 2 | $T_2$ | 20 | 22 | 56 | 136 |
| 24 hours | $T_1$ | 0.279 | 0.494 | 0.735 | 1.084 |
| N = 2 | $T_2$ | 22 | 44 | 68 | 155 |
| 7 days | $T_1$ | 0.268 | 0.572 | 0.712 | 0.972 |
| N = 2 | $T_2$ | 31 | 49 | 68 | 162 |

[1]N is the number of rats examined.

The data suggest that both the blood and the lung rapidly clear the magnetic material exhibting nearly no effect on the relaxation times 90 minutes after the injection. The spleen demonstrates a moderately rapid recovery, exhibiting a substantial reduction in both T1 and T2 90 minutes after the injection, but nearly no residual effect after 24 hours. The liver exhibits two different recovery rates. T1 attains its original value after 24 hours, while T2 remains substantially reduced after 24 hours and exhibits recovery after 7 days.

6.8. Comparative Biodistribution of Uncoated and Dextranized Particles

In this experimental series, the biodistribution of three uncoated and four dextran-coated particles was examined. The uncoated agents were produced according to the procedure of Section 6.3., the dextran-coated particles were produced according to the procedure of Section 6.1. except that the molecular weight of the dextran used for the coating was varied (See the Table II). Prior to each experiment, the contrast agents were dialyzed against distilled water and subsequently injected into separate groups of Sprague-Dawley rats in a distilled water carrier. The rats were periodically sacrificed and the relaxation times of the liver, spleen, and lung were determined on an IBM PC-20 NMR Spectrometer. Preprogrammed inversion recovery and Carr, Purcell, Meiboom, Gill pulse sequences were used to determine T1 and T2, respectively.

The results were as follows:

TABLE II

| Complex | Coating | Dose ($Fe_3O_4$) | Time After Dose | | Relaxation Times (msec.) | | |
|---|---|---|---|---|---|---|---|
| | | | | | Liver | Spleen | Lung |
| Control | — | None | — | $T_1$ | 0.27 | 0.54 | 0.717 |
| | | | | $T_2$ | 32 | 48 | 64 |
| AMI-12 | None | 24.2 μmoles/kg | 2.5 hr. | $T_1$ | 0.222 | 0.420 | 0.626 |
| | | | | $T_2$ | 22.7 | 26.0 | 45.8 |
| | | | 18 hr. | $T_1$ | 0.254 | 0.532 | 0.752 |
| | | | | $T_2$ | 29.6 | 42.9 | 68.2 |
| | | | 1 wk. | $T_1$ | 0.239 | 0.528 | 0.730 |
| | | | | $T_2$ | 31.6 | 43.8 | 72.0 |
| | | | 2 wk. | $T_1$ | 0.240 | 0.462 | 0.702 |
| | | | | $T_2$ | 29.4 | 35.5 | 79.5 |
| AMI-13 | None | 24.6 μmoles/kg | 2.5 hr. | $T_1$ | 0.221 | 0.424 | 0.672 |
| | | | | $T_2$ | 16.9 | 28.0 | 65.2 |
| | | | 18 hr. | $T_1$ | 0.218 | 0.386 | 0.802 |
| | | | | $T_2$ | 18.8 | 29.0 | 80.8 |
| | | | 1 wk. | $T_1$ | 0.236 | 0.443 | 1.753 |
| | | | | $T_2$ | 26.0 | 38.5 | 80.4 |
| | | | 2 wk. | $T_1$ | 0.236 | 0.493 | 0.722 |
| | | | | $T_2$ | 28.2 | 43.8 | 80.8 |
| AMI-14 | None | 25.4 μmoles/kg | 2 hr. | $T_1$ | 0.238 | 0.470 | 0.706 |
| | | | | $T_2$ | 20.8 | 31.8 | 72.4 |
| | | | 18 hr. | $T_1$ | 0.238 | 0.436 | 0.750 |
| | | | | $T_2$ | 20.4 | 34.7 | 69.6 |
| | | | 1 wk. | $T_1$ | 0.216 | 0.522 | 0.755 |
| | | | | $T_2$ | 26.7 | 41.7 | 80.4 |
| | | | 2 wk. | $T_1$ | 0.227 | 0.452 | 0.698 |
| | | | | $T_2$ | 24.8 | 43.6 | 78.7 |
| AMI-15 | Dextran 9,000 | 36.8 μmoles/kg | 4 hr. | $T_1$ | 0.238 | 0.300 | 0.672 |
| | | | | $T_2$ | 17.8 | 19.4 | 56.4 |

TABLE II-continued

| Complex | Coating | Dose ($Fe_3O_4$) | Time After Dose | | Relaxation Times (msec.) | | |
|---|---|---|---|---|---|---|---|
| | | | | | Liver | Spleen | Lung |
| | | | 24 hr. | $T_1$ | 0.253 | 0.387 | 0.740 |
| | | | | $T_2$ | 21.1 | 26.4 | 73.2 |
| | | | 1 wk. | $T_1$ | 0.219 | 0.485 | 0.766 |
| | | | | $T_2$ | 25.6 | 36.7 | 78.1 |
| | | | 2 wk. | $T_1$ | 0.258 | 0.523 | 0.718 |
| | | | | $T_2$ | 28.7 | 39.1 | 69.9 |
| AMI-16 | Dextran 17,900 | 32.4 μmoles/kg | 4 hr. | $T_1$ | 0.248 | 0.302 | 0.678 |
| | | | | $T_2$ | 18.8 | 16.5 | 56.2 |
| | | | 24 hr. | $T_1$ | 0.238 | 0.384 | 0.703 |
| | | | | $T_2$ | 19.9 | 24.9 | 71.6 |
| | | | 1 wk. | $T_1$ | 0.197 | 0.470 | 0.725 |
| | | | | $T_2$ | 25.3 | 37.1 | 74.6 |
| | | | 2 wk. | $T_1$ | 0.258 | 0.525 | 0.731 |
| | | | | $T_2$ | 28.9 | 44.8 | 73.3 |
| AMI-17 | Dextran 35,600 | 33.1 μmoles/kg | 4 hr. | $T_1$ | 0.244 | 0.318 | 0.674 |
| | | | | $T_2$ | 16.0 | 17.4 | 54.4 |
| | | | 24 hr. | $T_1$ | 0.247 | 0.388 | 0.690 |
| | | | | $T_2$ | 20.2 | 22.9 | 76.4 |
| | | | 1 wk. | $T_1$ | 0.214 | 0.500 | 0.696 |
| | | | | $T_2$ | 24.3 | 44.0 | 76.0 |
| | | | 2 wk. | $T_1$ | 0.244 | 0.562 | 0.726 |
| | | | | $T_2$ | 28.6 | 48.6 | 70.6 |
| AMI-18 | Dextran 249,000 | 39.2 μmoles/kg | 4 hr. | $T_1$ | 0.228 | 0.237 | 0.526 |
| | | | | $T_2$ | 20.0 | 17.7 | 58.6 |
| | | | 24 hr. | $T_1$ | 0.238 | 0.354 | 0.654 |
| | | | | $T_2$ | 21.0 | 22.0 | 68.2 |
| | | | 1 wk. | $T_1$ | 0.235 | 0.492 | 0.645 |
| | | | | $T_2$ | 31.4 | 36.1 | 71.3 |
| | | | 2 wk. | $T_1$ | 0.240 | 0.52 | 0.748 |
| | | | | $T_2$ | 31.0 | 39.8 | 71.3 |

As before, the data suggest that the contrast agents are rapidly cleared from the lung, and are longer lived in the spleen and the liver. Additionally, it can be seen that the dextranized complexes are cleared less rapidly than the uncoated ones, exerting a significant effect on the T2 values of the liver and spleen for about one week.

6.9. Physiologically Acceptable Carriers for GI Administration

The following mixtures are carriers which are suitable for use when the particles are administered into the gastrointestinal tract:

TABLE III

Suitable Carriers for Administration to the GI Tract 1. 18.25 gm sodium polymetaphosphate
   1.0 gm saccharin sodium
   0.75 gm methyl parahydroxybenzoate
   1.0 gm potassium sorbate
   3.0 gm xanthan gum
   2.0 gm peppermint oil
   971.0 gm water
2. 5.0 gm magnesium aluminium silicate
   478.0 gm liquid sorbitol 70%
   1.0 gm citric acid
   0.8 gm methyl parahydroxy-benzoate
   0.2 gm orange essence
   15.0 gm ethanol
   498.6 gm water
3. 10.0 gm hydroxyethyl cellulose
   0.8 gm methyl parahydroxy-benzoate
   0.2 gm propyl parahydroxybenzoate
   10.0 gm ethanol
   1.0 gm saccharin sodium
   0.3 gm orange essence
   0.7 gm apricot essence
   967.0 gm water
4. 0.5 gm polyoxyethylene/polyoxypropylene copolymer
   0.9 gm sodium chloride
   100 ml sterile water
5. 1.0 gm cellulose gum
   0.5 gm sodium chloride
   0.1 gm methyl parahydroxybenzoate

TABLE III-continued

Suitable Carriers for Administration to the GI Tract 2.0 gm ethanol
0.5 gm peppermint oil
96.0 gm water It is apparent that many modifications and variations of this invention as hereinabove set forth may be made without departing from the spirit and scope thereof. The specific embodiments described are given by way of example only and the invention is limited only by the terms of the appended claims.

We claim:

1. An improved method for obtaining an in vivo NMR image or an organ or tissue of an animal or human subject, wherein the improvement comprises administering to such a subject as a contrast agent to enhance such NMR image an effective amount of a dispersoid which comprises uncoated, biodegradable superparamagnetic metal oxide particles dispersed in a physiologically acceptable carrier, an individual particle (i) comprising one or more biodegradable metal oxide crystals, each crystal about 10 to about 500 angstroms in diameter; (ii) having an overall means diameter of about 10 angstroms to about 5000 angstroms as measured on a Coulter particle size analyzer; and (iii) further characterized as having a retention time in said organ or tissue sufficiently long to permit an image to be obtained and being ultimately biodegraded in said organ or tissue within a period of about 7 days.

2. An improved method for obtaining an in vivo NMR image of an organ or tissue of an animal or human subject, wherein the improvememt comprises administering to such a subject as a contrast agent to enhance such NMR image an effective amount of a dispersoid which comprises coated, biodegradable superparamagnetic metal oxide particles dispersed in a physiologically acceptable carrier, an individual particle (i) comprising a superparamagnetic metal oxide core generally surrounded by a biodegradable polymeric coat, each core comprising one or more biodegradable metal oxide crystals, each crystal about 10 to about 500 angstroms in diameter; (ii) having an overll mean diameter, inclusive of the polymeric coat, of about 10 to about 5000 angstroms as measured on a Coulter particle size analyzer; an (iii) further characterized as having a retention time in said organ or tissue sufficiently long to permit an image to be obtained and being ultimately biodegraded in said organ or tissue within a period of about 7 days.

3. The method of claim 1 or 2 wherein the superparamagetic metal oxide particle is an iron oxide particle (i) comprising crystals of about 50 to about 500 angstroms in diameter; (ii) having a surface area greater than about 75 $m^2$/gram; (iii) having a magnetic saturation between about 5 and about 50 EMU/gram of iron oxide; and (iv) possessing a magnetic squareness of less than 0.1.

4. The method of claim 2 wherein the polymeric coat is selected from the group consisting of carbohydrates, proteins, and composites thereof.

5. The method of claim 2 wherein the polymeric coat consists of albumin.

6. The method of claim 5 wherein the albumin is selected from the group consisting of human serum albumin and bovine serum albumin.

7. The method of claim 2 wherein the polymeric coat consists of dextran having a molecular weight between 5,000 and 250,000 daltons.

8. The method of claim 7 wherein the dextran is selected from the group consisting of dextran of 9,000 MW, dextran of 17,900 MW, dextran of 35,600 MW, dextran of 71,000 MW and dextran of 249,000 MW.

9. The method of claim 1 or 2 wherein said dispersoid is administered to the subject by intravascular injection.

10. The method of claim 1 or 2 wherein said dispersoid is administered to the subject by a method selected from the group consisting of oral administration, intubation, and by enema.

11. The method of claim 9 wherein the physiologically acceptable carrier is selected from the group consisting of normal saline and distilled water.

12. The method of claim 10 wherein said physiologically acceptable carrier is distilled water.

13. The method of claim 1 or 2 wherein the superparamagnetic metal oxide particles are administered at a dosage of up to about 250 mg per Kilogram of body weight of the subject.

14. The method of claim 1 or 2 wherein the organ or tissue imaged is part of the reticuloendothelial system.

15. The method of claim 14 wherein the organ imaged is a liver.

16. The method of claim 14 wherein the organ imaged is a spleen.

17. The method of claim 14 wherein the tissue imaged is bone marrow.

18. The method of claim 14 wherein the organ or tissue imaged is lymph or lymph nodes.

19. The method of claim 1 or 2 wherein the tissue imaged is neural tissue.

20. The method of claim 1 or 2 wherein the organ imaged is a lung.

21. The method of claim 1 or 2 wherein the organ or tissue imaged is part of the gastrointestinal tract.

22. The method of claim 21 wherein the organ imaged is an esophagus.

23. The method of claim 21 wherein the organ imaged is a stomach.

24. The method of claim 21 wherein the organ imaged is a small intestine.

25. The method of claim 21 wherein the organ imaged is a large intestine.

* * * * *

UNITED STATES PATENT AND TRADEMARK OFFICE
CERTIFICATE OF CORRECTION

PATENT NO. : 4,770,183
DATED : September 13, 1988
INVENTOR(S) : Ernest V. Groman et al.

It is certified that error appears in the above-identified patent and that said Letters Patent is hereby corrected as shown below:

Col. 16, line 46, "or an" should read --of an--;

Col. 17, line 8, "an (iii)" should read --and (iii)--.

Signed and Sealed this

Fourteenth Day of February, 1989

Attest:

DONALD J. QUIGG

*Attesting Officer*    *Commissioner of Patents and Trademarks*